United States Patent [19]

Hayes

[11] 4,048,099

[45] Sept. 13, 1977

[54] HYDROCARBON CONVERSION WITH AN ACIDIC TRIMETALLIC CATALYTIC COMPOSITE

[75] Inventor: John C. Hayes, Palatine, Ill.

[73] Assignee: UOP Inc., Des Plaines, Ill.

[21] Appl. No.: 615,647

[22] Filed: Sept. 22, 1975

Related U.S. Application Data

[60] Division of Ser. No. 442,714, Feb. 14, 1974, Pat. No. 3,928,177, which is a continuation-in-part of Ser. No. 216,739, Jan. 10, 1972, Pat. No. 3,806,446, which is a division of Ser. No. 17,886, March 9, 1970, abandoned.

[51] Int. Cl.$^2$ .................. B01J 27/06; B01J 27/02; C10G 35/06
[52] U.S. Cl. .................................. 252/441; 252/439; 252/442; 208/139
[58] Field of Search .................... 252/439, 441, 442

[56] References Cited

U.S. PATENT DOCUMENTS

| | | | |
|---|---|---|---|
| 2,378,209 | 6/1945 | Fuller et al. | 260/673.5 |
| 2,441,297 | 5/1948 | Stirton | 260/668 R |
| 2,500,146 | 3/1950 | Fleck et al. | 260/668 |
| 2,906,700 | 9/1959 | Stine | 208/138 |
| 3,003,972 | 10/1961 | Haensel | 252/441 |
| 3,017,369 | 1/1962 | Nixon | 252/441 |
| 3,272,760 | 9/1966 | Doelp, Jr. | 252/465 |
| 3,531,543 | 9/1970 | Clippinger et al. | 260/683.3 |
| 3,544,452 | 12/1970 | Jaffe | 252/441 X |
| 3,576,766 | 4/1971 | Rausch | 252/439 |
| 3,578,584 | 5/1971 | Hayes | 252/442 X |
| 3,630,961 | 12/1971 | Wilhelm | 252/442 X |
| 3,652,697 | 3/1972 | Hayes | 252/442 X |
| 3,654,184 | 4/1972 | McCallister et al. | 252/441 X |
| 3,711,425 | 1/1973 | Suggitt et al. | 252/442 X |

*Primary Examiner*—Patrick P. Garvin
*Assistant Examiner*—William G. Wright
*Attorney, Agent, or Firm*—James R. Hoatson, Jr.; Thomas K. McBride; William H. Page, II

[57] ABSTRACT

Hydrocarbons are converted by contacting them at hydrocarbon conversion conditions with an acidic trimetallic catalytic composite comprising a combination of catalytically effective amounts of a platinum group component, a Group IV-A metallic component, a Group VI-B transition metal component and a halogen component with a porous carrier material. The platinum group component, Group IV-A metallic component, and halogen component are present in the trimetallic catalyst in amounts respectively, calculated on an elemental basis, corresponding to about 0.01 to about 2 wt. % platinum group metal, about 0.01 to about 5 wt. % Group IV-A metal and about 0.1 to about 3.5 wt. % halogen. The Group VI-B component is present in an amount of about 0.01 to about 3 wt. % and the atomic ratio of Group VI-B metal to platinum group metal is about 0.05:1 to about 4:1. Moreover, these metallic components are uniformly dispersed throughout the porous carrier material in carefully controlled oxidation states such that substantially all of the platinum group metal is present therein in the elemental metallic state; while substantially all of the Group IV-A metallic component and all of the Group VI-B component are present therein in an oxidation state above that of the corresponding metal.

15 Claims, No Drawings

HYDROCARBON CONVERSION WITH AN ACIDIC TRIMETALLIC CATALYTIC COMPOSITE

CROSS-REFERENCES TO RELATED APPLICATIONS

This application is a division of my prior, copending application Ser. No. 442,714 filed Feb. 14, 1974 now U.S. Pat. No. 3,928,177; which in turn is a continuation-in-part of my prior, copending application Ser. No. 216,739 filed Jan. 10, 1972 and now U.S. Pat. No. 3,806,446; which in turn is a division of my prior application Ser. No. 17,886 filed on Mar. 9, 1970 and now abandoned. All of the teachings of these prior applications are specifically incorporated herein by reference.

The subject of the present invention is a novel acidic trimetallic catalytic composite which has exceptional activity and resistance to deactivation when employed in a hydrocarbon conversion process that requires a catalyst having both a hydrogenation-dehydrogenation function and a selective cracking function. More precisely, the present invention involves a novel dual-function acidic trimetallic catalytic composite which, quite surprisingly, enables substantial improvements in hydrocarbon conversion processes that have traditionally used a dual-function catalyst. In another aspect, the present invention comprehends the improved processes that are produced by the use of a catalytic composite comprising a combination of catalytically effective amounts of a platinum group component, a Group VI-B transition metal component, a Group IV-A metallic component and a halogen component with a porous carrier material; specifically, an improved reforming process which utilizes the subject catalyst to improve activity, selectivity, and stability characteristics.

Composites having a hydrogenation-dehydrogenation function and a cracking function are widely used today as catalysts in many industries, such as the petroleum and petrochemical industry, to accelerate a wide spectrum of hydrocarbon conversion reactions. Generally, the cracking function is thought to be associated with an acid-acting material of the porous, adsorptive, refractory oxide type which is typically utilized as the support or carrier for a heavy metal component such as the transition metals or compounds of the transition metals of Groups V through VIII of the Periodic Table to which are generally attributed the hydrogenation-dehydrogenation function.

These catalytic composites are used to accelerate a wide variety of hydrocarbon conversion reactions such as hydrocracking, isomerization, dehydrogenation, hydrogenation, desulfurization, cyclization, alkylation, polymerization, cracking, hydroisomerization, etc. In many cases, the commercial applications of these catalysts are in processes where more than one of these reactions are proceeding simultaneously. An example of this type of process is reforming wherein a hyrocarbon feed stream containing paraffins and naphthenes is subjected to conditions which promote dehydrogenation of naphthenes to aromatics, dehydrocyclization of paraffins to aromatics, isomerization of paraffins and naphthenes, hydrocracking of naphthenes and paraffins and the like reactions, to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffins is contacted with a dual-function catalyst in the presence of hydrogen to produce an output stream rich in isoparaffins.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity and stability. And for purposes of discussion here, these terms are conveniently defined for a given charge stock as follows: (1) activity is a measure of the catalyst's ability to convert hydrocarbon reactants into products at a specified severity level where severity level means the reaction conditions used — that is, the temperature, pressure, contact time, and presence of diluents such as $H_2$; (2) selectivity refers to the amount of desired product or products obtained relative to the amount of reactants charged or converted; (3) stability refers to the rate of change with time of activity and selectivity parameters — obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield, relative to the amount of the charge, that is obtained at the particular activity or severity level; and stability is typically equated to the rate of change with time of activity, as measured by octane number of $C_5+$ product, and of selectivity, as measured by $C_5+$ yield. Actually, this last statement is not strictly correct because generally a continuous reforming process is run to produce a constant octane $C_5+$ product with severity level being continuously adjusted to attain this result; and, furthermore, the severity level is for this process usually varied by adjusting the conversion temperature in the reaction zone so that, in point of fact, the rate of change of activity finds response in the rate of change of conversion temperature and changes in this last parameter are customarily taken as indicative of activity-stability.

As is well known to those skilled in the art, the principal cause of observed deactivation or instability of a dual-function catalyst when it is used in a hydrocarbon conversion reaction is associated with the fact that coke forms on the surface of the catalyst during the course of the reaction. More specifically, in these hydrocarbon conversion processes, the conditions utilized typically result in the formation of heavy, high molecular weight, black, solid or semi-solid, carbonaceous material which coats the surface of the catalyst and reduced its activity by shielding its active sites from the reactants. In other words, the performance of this dual-function catalyst is sensitive to the presence of carbonaceous deposits on the surface of the catalyst. Accordingly, the major problem facing workers in this area of the art is the development of more active and selective catalytic composites that are not as sensitive to the presence of these carbonaceous materials and/or have the capability to suppress the rate of the formation of these carbonaceous materials on the catalyst. Viewed in terms of performance parameters, the problem is to develop a dual-function catalyst having superior activity, selectivity and stability. In particular, for a reforming process the problem is typically expressed in terms of shifting and stabilizing the $C_5+$ yield-octane relationship — $C_5+$ yield being representative of selectivity and octane being proportional to activity.

I have now found a dual-function acidic trimetallic catalytic composite which possesses improved activity, selectivity and stability characteristics when it is employed in a process for the conversion of hydrocarbons of the type which have heretofore utilized dual-function acidic catalytic composites such as processes for isomerization, hydroisomerization, dehydrogenation, desulfurization, denitrogenization, hydrogenation, alkylation, dealkylation, hydrodealkylation, transalkylation, cyclization, dehydrocyclization, cracking, hydrocracking, reforming disproportionation, polymerization, halogenation, and the like processes. In particular, I have ascertained that the use of an acidic catalyst, comprising a combination of catalytically effective amounts of a platinum group component, a Group VI-B transition metal component, a Group IV-A metallic component and a halogen component with a porous refractory carrier material, can enable the performance of hydrocarbon conversion processes utilizing dual-function catalysts to be substantially improved if the metallic components are uniformly dispersed throughout the carrier material in the hereinafter specified amounts and if their oxidation states are controlled to be in the states hereinafter specified. Moreover, I have determined that an acidic catalytic composite, comprising a combination of catalytically effective amounts of a platinum group component, a Group VI-B metallic component, a Group IV-A metallic component and a chloride component with an alumina carrier material, can be utilized to substantially improve the performance of a reforming process which operates on a low-octane gasoline fraction to produce a high-octane reformate if the metallic components are uniformly distributed throughout the alumina carrier material in the proper amounts and in their oxidation states are fixed in the states hereinafter specified. In the case of a reforming process, the principal advantage associated with the use of the novel catalyst of the present invention involves the acquisition of the capability to operate in a stable manner in a high severity operation; for example, a low pressure reforming process designed to produce a high yield of $C_5+$ reformate having an octane of about 100 F-1 clear. As indicated, the present invention essentially involves the finding that the addition of a combination of a Group IV-A metallic component and of a Group VI-B metallic component to a dual-function acidic hydrocarbon conversion catalyst containing a platinum group component can enable the performance of the resulting catalyst to be sharply and materially improved, if the hereinafter specified limitations on amounts of ingredients, oxidation states of metals and distribution of metallic components in the support are met.

It is, accordingly, one object of the present invention to provide an acidic trimetallic hydrocarbon conversion catalyst having superior performance characteristics when utilized in a hydrocarbon conversion process. A second object is to provide an acidic trimetallic catalyst having dual-function hydrocarbon conversion performance characteristics that are relatively insensitive to the deposition of hydrocarbonaceous material thereon. A third object is to provide preferred methods of preparation of this acidic catalytic composite which insures the achievement and maintenance of its properties. Another object is to provide an improved reforming catalyst having superior activity, selectivity and stability characteristics. Yet another object is to provide a dual-function hydrocarbon conversion catalyst which utilizes a combination of a Group IV-A metallic component and a Group VI-B metallic component to promote an acidic catalyst containing a platinum or palladium or iridium metal component.

In brief summary, the present invention is, in one embodiment, an acidic catalytic composite comprising a porous carrier material containing, on an elemental basis, about 0.01 to about 2 wt. % platinum group metal, about 0.1 to about 3.5 wt. % halogen, about 0.01 to about 5 wt. % Group IV-A metal and about 0.01 to about 3 wt. % Group VI-B transition metal; wherein the platinum group metal, Group VI-B metal, and Group IV-A metal are uniformly dispersed throughout the porous carrier material; wherein substantially all of the platinum group metal is present in the elemental metallic state; wherein substantially all of the Group IV-A metal and all of the Group VI-B transition metal are present in an oxidation state above that of the corresponding elemental metal; wherein the halogen component is present in the form of the combined halide; and wherein the atomic ratio of Group VI-B metal to platinum group metal is about 0.05:1 to about 4:1.

A second embodiment relates to an acidic catalytic composite comprising a porous carrier material containing, on an elemental basis, a uniform dispersion of about 0.05 to about 1 wt. % platinum or palladium or iridium metal, about 0.5 to about 1.5 wt. % halogen, about 0.05 to about 2 wt. % Group IV-A metal and about 0.05 to about 1 wt. % Group VI-B transition metal; wherein the atomic ratio of Group VI-B metal to platinum or palladium or iridium metal is about 0.05:1 to about 4:1; wherein the platinum or palladium or iridium is present in the corresponding elemental metallic state; wherein substantially all of the Group IV-A metal is present in an oxidation state above that of the elemental metal; wherein substantially all of the Group VI-B transition metal is present in an oxidation state above that of the elemental metal; and wherein the halogen is present in the form of the combined halide.

Another embodiment relates to a catalytic composite comprising a combination of the catalytic composite described in the first or second embodiments with a sulfur component in an amount sufficient to incorporate about 0.05 to about 0.5 wt. % sulfur, calculated on an elemental basis.

Yet another embodiment relates to a process for the conversion of a hydrocarbon comprising contacting the hydrocarbon and hydrogen with the catalytic composite described above in the first, second or third embodiments at hydrocarbon conversion conditions.

A preferred embodiment relates to a process for reforming a gasoline fraction which comprises contacting the gasoline fraction and hydrogen with the catalytic composite described above in the first, second or third embodiments at reforming conditions selected to produce a high-octane reformate.

Other objects and embodiments of the present invention relate to additional details regarding preferred catalytic ingredients, preferred amounts of ingredients, suitable methods of composite preparation, operating conditions for use in the hydrocarbon conversion processes, and the like particulars which are hereinafter given in the following detailed discussion of each of these facets of the present invention.

The acidic trimetallic catalyst of the present invention comprises a porous carrier material or support having combined therewith catalytically effective amounts of a platinum group component, a Group VI-B transition metal component, a Group IV-A metallic component, and a halogen component.

Considering first the porous carrier material utilized in the present invention, it is preferred that the material be a porous, adsorptive, high-surface area support having a surface area of about 25 to about 500 m²/g. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke or charcoal; (2) silica or silica gel, silicon carbide, clays and silicates including those synthetically-prepared and naturally-occuring, which may or may not be acid treated, for example, attapulgus clay, china clay, diatomaceous earth, fuller's earth, kaoline, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally-occurring or synthetically-prepared mordenite and/or faujasite, either in the hydrogen form or in a form which has been treated with multivalent cations; (6) spinels such as $MgAl_2O_4$, $FeAl_2O_4$, $ZnAl_2O_4$, $CaAl_2O_4$ and other like compounds having the formula $MO.Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline aluminas known as the gamma-, eta- and theta-alumina, with gamma- or eta-alumina giving best results. In addition, in some embodiments the alumina carrier material may contain minor proportions of other well known refractory inorganic oxides such as silica, zirconia, magnesia, etc.; however, the preferred support is substantially pure gamma-, or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 m²/g. In general, best results are typically obtained with a gamma-alumina carrier material which is used in the form of spherical particles having: a relatively small diameter (i.e., typically about 1/16 inch), an apparent bulk density of about 0.5 to about 0.6 g/cc, a pore volume of about 0.4 cc/g, and a surface area of about 175 m²/g.

The preferred alumina carrier material may be prepared in any suitable manner and may be synthetically-prepared or natural occurring. Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the instant multimetallic catalytic composite is the Group IV-A metallic component. By the use of the generic term "Group IV-A metallic component" it is intended to cover the metal of Group IV-A of the Periodic Table. More specifically it is intended to cover: germanium, tin, lead and mixtures of these metals. It is an essential feature of the present invention that substantially all of the Group IV-A metallic component is present in the final catalyst in an oxidation state above that of the elemental metal. In other words, this component may be present in chemical combination with one or more of the other ingredients of the composite, or as a chemical compound of the Group IV-A metal such as the oxide, sulfide, halide, oxyhalide, oxychloride, aluminate, and the like compounds. Based on the evidence currently available, it is believed that best results are obtained when substantially all of the Group IV-A metallic component exists in the final composite in the form of the corresponding oxide such as the tin oxide, germanium oxide, and lead oxide, and the subsequently described oxidation and reduction steps, that are preferably used in the preparation of the instant composite, are believed to result in a catalytic composite which contains an oxide of the Group IV-A metallic component. Regardless of the state in which this component exists in the composite, it can be utilized therein in any amount which is catalytically effective, with the preferred amount being about 0.01 to about 5 wt. % thereof, calculated on an elemental basis, and the most preferred amount being about 0.05 to about 2 wt. %. The exact amount selected within this broad range is preferably determined as a function of the particular Group IV-A metal that is utilized. For instance, in the case where this component is lead, it is preferred to select the amount of this component from the low end of the range — namely, about 0.01 to about 1 wt. %. Additionally, it is preferred to select the amount of lead as a function of the amount of the platinum group component as explained hereinafter. In the case where this component is tin, it is preferred to select from a relatively broader range of about 0.05 to about 2 wt. % thereof. And, in the preferred case, where this component is germanium the selection can be made from the full breadth of the stated range — specifically, about 0.01 to about 5 wt. %, with best results at about 0.05 to about 2 wt. %.

This Group IV-A component may be incorporated in the composite in any suitable manner known to the art to result in a uniform dispersion of the Group IV-A moeity throughout the carrier material such as, coprecipitation or cogellation with the porous carrier material, ion exchange with the carrier material, or impregnation of the carrier material at any stage in its preparation. It is to be noted that it is intended to include within the scope of the present invention all conventional procedures for incorporating a metallic component in a catalytic composite, and the particular method of incorporation used is not deemed to be an essential feature of the present invention so long as the Group IV-A component is uniformly dispersed throughout the porous carrier material. One acceptable method of incorporating the Group IV-A component into the catalytic composite involves cogelling the Group IV-A component during the preparation of the preferred carrier material, alumina. This method typically involves the addition of a suitable soluble compound of the Group IV-A metal of interest to the alumina hydrosol. The resulting mixture is then commingled with a suitable gelling agent, such as a relatively weak alkaline reagent, and the resulting mixture is thereafter preferably gelled by dropping into a hot oil bath as explained hereinbefore. After aging, drying and calcining the resulting particles there is obtained an intimate combination of the oxide of the Group IV-A metal and alumina. One preferred method of incorporating this component into the composite involves utilization of a soluble decomposable compound of the particular Group IV-A metal of interest to impregnate the porous carrier material either before, during or after the carrier material is calcined. In general, the solvent used during this impregnation step is selected on the basis of its capability to dissolve the desired Group IV-A compound without effecting the porous carrier material which is to be impregnated; ordinarily, good results are obtained when water is the solvent; thus the preferred Group IV-A compounds for use in this impregnation step are typically water-soluble and decomposable. Examples of suitable Group IV-A compounds are: germanium difluoride, germanium tetra-alkoxide, germanium dioxide, germanium tetrafluoride, germanium monosulfide, tin chloride, tin bromide, tin dibromide di-iodide, tin dichloride di-iodide, tin chromate, tin difluoride, tin tetrafluoride, tin tetraiodide, tin sulfate, tin tartrate, lead acetate, lead bromate, lead chlorate, lead chloride, lead citrate, lead formate, lead lactate, lead malate, lead nitrate, lead nitrite, lead dithionate, and the like compounds. In the case where the Group IV-A component is germanium, a preferred impregnation solution is germanium tetrachloride dissolved in anhydrous alcohol. In the case of tin, tin chloride dissolved in water is preferred. In the case of lead, lead nitrate dissolved in water is preferred. Regardless of which impregnation solution is utilized, the Group IV-A component can be impregnated either prior to, simultaneously with, or after the other metallic components are added to the carrier material. Ordinarily, best results are obtained when this component is impregnated simultaneously with the other metallic components of the composite. Likewise, best results are ordinarily obtained when the Group IV-A component is germanium oxide or tin oxide.

Regardless of which Group IV-A compound is used in the preferred impregnation step; it is essential that the Group IV-A metallic component by uniformly distributed throughout the carrier material. In order to achieve this objective when this component is incorporated by impregnation, it is necessary to maintain the pH of the impregnation solution at a relatively low level corresponding to about 7 to about 1 or less and to dilute the impregnation solution to a volume which is at least approximately the same or greater than the volume of the carrier material which is impregnated. It is preferred to use a volume ratio of impregnation solution to carrier material of at least 1:1 and preferably about 2:1 to about 10:1 or more. Similarly, it is preferred to use a relatively long contact time during the impregnation step ranging from about $\frac{1}{4}$ hour up to about $\frac{1}{2}$ hour or more before drying to remove excess solvent in order to insure a high dispersion of the Group IV-A metallic component in the carrier material. The carrier material is, likewise, preferably constantly agitated during this preferred impregnation step.

A second essential ingredient of the subject catalyst is the platinum group component. That is, it is intended to cover the use of platinum or palladium or iridium or rhodium or osmium or ruthenium or mixtures thereof as a second component of the present composite. It is an essential feature of the present invention that substantially all of the platinum group component exists within the final catalytic composite in the elemental metallic state (i.e., as elemental platinum or palladium or iridium etc.). Generally the amount of the second component used in the final composite is relatively small compared to the amount of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of platinum, iridium or palladium metal.

This platinum group metal component may be incorporated in the catalytic composite in any suitable manner known to result in a relatively uniform distribution of this component in the carrier material such as coprecipitation or cogellation, ion-exchange, or impregnation. The preferred method of preparing the catalyst involves the utilization of a soluble, decomposable compound of a platinum group metal to impregnate the carrier material in a relatively uniform manner. For example, this component may be added to the support by commingling the latter with an aqueous solution of chloroplatinic, chloroiridic or chloropalladic acid. Other water-soluble compounds of platinum group metals may be employed in impregnation solutions and include ammonium chloroplatinate, bromoplatinic acid, platinum dichloride, platinum tetrachloride hydrate, platinum dichlorocarbonul dichloride, dinitrodiaminoplatinum, tetramine platinum chloride, palladium chloride, palladium nitrate, palladium sulfate, etc. The utilization of a platinum group metal chloride compound, such as chloroplatinic, chloroiridic or chloropalladic acid, is preferred since it facilitates the incorporation of both the platinum group component and at least a minor quantity of the halogen component in a single step. Hydrogen chloride or the like acid is also generally added to the impregnation solution in order to further facilitate the incorporation of the halogen component and the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Another essential ingredient of the instant catalyst is a Group VI-B transisiton metal component. Elements included within the scope of this expression are chromium, molybdenum and tungsten, with tungsten being especially preferred. This component may exist within the final catalyst composite in any form wherein substantially all of the Group VI-B metal moiety is present in an oxidation state above that of the corresponding metal such as in a compound like the corresponding oxide, sulfide, halide, oxyhalide, aluminate, or in chemical combination with one or more of the other ingreidents of the composite. Best results are obtained when susbstantially all of this component is present in the composite as the corresponding Group VI-B metal oxide. It is preferred that the final composite contain about 0.01 to about 3 wt. % of this component, calculated on an elemental basis with the most preferred range being about 0.05 to about 1wt. %. A particulary preferred catalyst, for example, would contain, on an elemental basis, about 0.05 to about 1 wt. % tungsten. The function performed by this component is not entirely understood; however, I believe its prime influence is that it acts in conjunction with the Group IV-A metallic component to promote and stabilize the platinum group component.

This Group VI-B transition metal component may be incorporated in the final composite in any suitable manner known to those skilled in the catalyst formulation art which results in a relatively uniform dispersion of the Group VI-B moiety in the carrier material. One method involves impregnation of the porous carrier material with a suitable solution of the Group VI-B transition metal at any stage in the preparation of the carrier material — that is, either as a hydrogel or after its calcination. Another method is the ion-exchanger method in which a soluion of a suitable compound of the Group VI-B transition metal, wherein the metal is present as an exchangeable ion, is contacted with the carrier material. Still another method involves cogellation or coprecipitation of the Group VI-B component with the carrier material. The preferred method involes impregnation of the calcined carrier material with a solution containing the Group VI-B transition metal; for example, excellent results are obtained by impregnating with aqueous solution of a suitable Group VI-B compound such as ammonium tungstate, sodium tungstate, metatungstic acid, molybdenum tetrabromide, molybdic acid, chromium dibromide, chromium dichloride, chromic acid, chromium nitrate, sodium chromate, ammonium molybdate, etc., followed by coventional drying and calcination or oxidation steps. Like the previous components, this component may be added before, during or after the addition of the other metallic components, with best results obtained with simultaneous addition. For example, in the case of the preferred platinum-germanium-tungsten catalyst, excellent results are obtained with an impregnation solution comprising a mixture of a first solution containing chloroplatinic acid, hydrochloric acid, and ammonium tungstate with a second solution containing germanium tetrachloride dissolved in anhydrous ethanol.

It is essential to incorporate a halogen component into the trimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g., as the chloride). This combined halogen may be either fluroine, chlorine, bromine, or mixtures thereof. Of these fluroine and, particularly, chlorine are preferred for the purpose of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the metallic components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5% and preferably about 0.5 to about 1.5% by weight of halogen, calculated on an elemental basis. In isomerization or hydrocracking embodiments, it is generally preferred to utilize relatively larger amounts of halogen in the catalyst — typically, ranging up to about 10 wt. % halogen calculated on an elemental basis, and more preferably about 1 to about 5 wt. %.

Regarding the preferred amounts of the various metallic components of the subject catalyst, I have found it to be an essential practice to specify the amounts of the Group VI-B component as a function of the amount of the platinum group component. On this basis, the amount of the Group VI-B component is selected from the ranges previously specified so that the atomic ratio of Group VI-B metal to the platinum group metal contained in the compoiste is about 0.05:1 to 4:1, with best results obtained when the range is about 0.1:1 to about 1:1. Similarly, it is a preferred practice to select the amount of the Group IV-A metallic component to produce a composite containing an atomic ratio of Group IV-A metal to platinum group metal within the broad range of about 0.05:1 to 10:1. However, for the Group IV-A metal to platinum group metal ratio, the best practice is to select this ratio on the basis of the following preferred ranges for the individual Group IV-A species: (1) for germanium, it is about 0.3:1 to 10:1, with the most preferred range being about 0.6:1 to about 6:1; (2) for tin, it is about 0.1:1 to 3:1, with the most preferred range being about 0.5:1 to 1.5:1; and, (3) for lead, it is about 0. 05:1 to 0.9:1, with the most preferred range being about 0.1:1 to 0.75:1.

Another significant parameter for the present catalyst is the "total metals content" which is defined to be the sum of the platinum group component, the Group VI-B component, and the Group IV-A metallic component, calculated on an elemental basis. Good results are ordinarily obtained with the subject catalyst when this parameter is fixed at a value of about 0.15 to about 4 wt. %, with best results ordinarily achieved at a metals loading of about 0.3 to about 2 wt. %.

In embodiments of the present invention wherein the instant trimetallic catalyst composite is used for the dehydrogenation of dehydrogentable hydrocarbons or for the hydrogenation of hydrogenatable hydrocarbons, it is ordinarily a preferred practice to include an alkali or alkaline earth metal component in the composite and to maintain the halogen component at the lowest possible value. More precisely, this optional component is selected, from the group consisting of the compounds of the alkali metals — cesium, rubidium, potassium, sodium, and lithium — and the compounds of the alkaline earth metals — calcium, strontium, barium and magnesium. Generally, good results are obtained in these embodiments when this component constitutes about 0.1 to about 5 wt. % of the composite, calculated on an elemental basis. This optional alkali or alkaline earth metal component can be incorporated in the composite in any of the known ways, with inpregnation with an aqueous solution of a suitable water-soluble, decomposable compound being preferred.

An optional ingredient for the trimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best resuls. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred.

Regardless of the details of how the components of the catalyst are combined with the porous carrier material, the final catalyst generally will be dried at a temperature of about 200° to about 600° F. for a period of at least about 2 to 24 hours or more, and finally calcined or oxidized at a temperature of about 700° F. to about 110° F. in an air atmosphere for a period of about 0.5 to about 10 hours in order to convert substantially all of the metallic components to the corresponding oxied forms. Because a halogen component is utilized in the catalyst, best results are generally obtained when the halogen content of the catalyst is adjusted during the calcination step by including a halogen or a halogen-containing compound in the air atmosphere utilized. In particular, when the halogen component of the catalyst is combined chloride, it is preferred to use a mole ratio of $H_2O$ to HCl of about 5:1 to about 100:1 during at least a portion of the calcination step in order to adjust the final chlorine content of the catalyst to a range of about 0.1 to about 3.5 wt. %.

It is an essential feature of the present invention that the resultant oxidized trimetallic catalytic composite is subjected to a substantially water-free reduction step prior to its use in the conversion of hydrocarbons. This step is designed to insure a uniform and finely divided dispersion of the metallic components throughout the carrier material and to selectively reduce the platinum group component to the corresponding metal while maintaining substantially all of the Group IV-A metallic component and the Group VI-B component in positive oxidation states. Preferably, substantially pure and dry hydrogen (i.e., less than 20 vol. ppm. $H_2O$) is used as the reducing agent in this step. The reducing agent is contacted with the oxidized catalyst at conditions including a temperature of about 800° F. to about 1200° F. and a period of time of about 0.5 to 2 hours effective to reduce substantially all of the platinum group component to the elemental metallic state while maintaining substantially all of the Group IV-A metallic component and the Group VI-B component in oxidation states above that of the corresponding elemental metals. This reduction treatment may be performed in situ as part of the start-up sequence if precautions are taken to predry the plant to a substantially water-free state and if substantially water-free hydrogen is used.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing and metallic sulfide-producing compound such as hydrogen sulfide, lower molecular weight mercaptans, organic sulfides, disulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more. It is generally a good practice to perform this presulfiding step under substantially water-free conditions.

According to the present invention, a hydrocarbon charge stock and hydrogen are contacted with an acidic trimetallic catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor-phase when they contact the catalyst, with best results obtained in the vapor phase.

In the case where the trimetallic catalyst of the present invention is used in a reforming operation, the reforming system will comprise a reforming zone containing a fixed bed of the catalyst type previously characterized. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° F. to about 150° F. and an end boiling point within the range of from about 325° F. to about 425° F., or may be a selected fraction thereof which generally will be a higher boiling fraction commonly referred to as a heavy naphtha — for example, a naphtha boiling in the range of $C_7$ to 400° F. In some cases, it is also advantageous to charge pure hydrocarbons or mixtures of hydrocarbons that have been extracted from hydrocarbon distillates — for example, straight-chain paraffins — which are to be converted to aromatics. It is preferred that these charge stocks be treated by conventional catalytic pretreatment methods such as hydrorefining, hydrotreating, hydrodesulfurization, etc., to remove substantially all sulfurous, nitrogenous and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment the charge stock can be a paraffinic stock rich in $C_4$ to $C_8$ normal paraffins, or a normal butane-rick stock, or an n-hexane-rick stock, or a mixture of xylene isomers, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromatic, a naphthene and the like. In hydrocracking embodiments, the charge stock will be typically a gas oil, heavy cracked cycle oil, etc. In addition, alkylaromatic and naphthenes can be conveniently isomerized by using the catalyst of the present invention. Likewise, pure hydrocarbons or substantially pure hydrocarbons can be converted to more valuable products by using the trimetallic catalyst of the present invention in any of the hydrocarbon conversion processes, known to the art, that use a dual-function catalyst.

In a reforming embodiment, it is generally preferred to utilize the novel trimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 50 ppm. and preferably less than 20 ppm.; expressed as weight of equivalent water in the charge stock. In general, this can be accomplished by careful control of the water present in the charge stock and in the hydrogen stream. The charge stock can be dried by using any suitable drying means known to the art such as a conventional solid adsorbent having a high selectivity for water; for instance, sodium or calcium crystalline aluminosilicates, silica-gel, activated alumina, molecular sieves, anhydrous calcium sulfate, high surface area sodium and the like adsorbent. Similarly, the water content of the charge stock may be adjusted by suitable stripping operations in a fractionation column or like device. And in some cases, a combination of adsorbent drying and distillation drying may be used advantageously to effect almost complete removal of water from the charge stock. Preferably, the charge stock is dried to a level corresponding to less than 20 ppm. of $H_2O$ equivalent. In general, it is preferred to maintain the hydrogen stream entering the hydrocarbon conversion zone at a level of about 10 vol. ppm. of water or less. In the case where the water content of hydrogen stream is above this range, this can be conveniently accomplished by contacting the hydrogen stream with a suitable desiccant such as those mentioned above at conventional drying conditions.

In the reforming embodiment, an effluent stream is withdrawn from the reforming zone and passed through a cooling means to a separation zone, typically maintained at about 25° to 150° F., wherein a hydrogen-rich gas is separated from a high octane liquid product, commonly called an "unstabilized reformate". When a superdry operation is desired, at least a portion of this hydrogen-rich gas is withdrawn from the separating zone and passed through an adsorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling front-end volatility of the resulting reformate.

The conditions utilized in the numberous hydrocarbon conversion embodiments of the present invention are those customarily used in the art for the particular reaction, or combination of reactions, that is to be effected. For instance, alkylaromatics and paraffin isomerization conditions include: a temperature of about 32° F. to about 1000° F. and preferably about 75° F. to about 600° F.; a pressure of atmospheric to about 100 atmospheres; a hydrogen to hydrocarbon mole ratio of about 0.5:1 to about 20:1 and a LHSV (calculated on the basis of equivalent liquid volume of the charge stock contacted with the catalyst per hour divided by the volume of conversion zone containing catalyst) of about 0.2 hr.$^{-1}$ to 10 hr.$^{-1}$. Dehydrogenation conditions include: a temperature of about 700° to about 1250° F., a pressure of about 0.1 to about 10 atmospheres, a liquid hourly space velocity of about 1 to 40 hr.$^{-1}$ and a hydrogen to hydrocarbon mole ratio of about 1:1 to 20:1. Likewise, typically hydrocracking conditions include: a pressure of about 500 psig. to about 3000 psig.; a temperature of about 400° F. to about 900° F.; a LHSV of about 0.1 hr.$^{-1}$ to about 10 hr.$^{-1}$, and hydrogen circulation rates of about 1000 to 10,000 SCF per barrel of charge.

In the reforming embodiment of the present invention the pressure utilized is selected from the range of about 0 psig. to about 1000 psig., with the preferred pressure being about 50 psig. to about 350 psig. Particularly good results are obtained at low pressure; namely, a pressure of about 75 to 250 psig. In fact, it is a singular advantage of the present invention that it allows stable operation at lower pressure than have heretofore been successfully utilized in so-called "continuous" reforming systems (i.e., reforming for periods of about 15 to about 200 or more barrels of charge per pound of catalyst without regeneration) with all platinum monometallic catalysts. In other words, the trimetallic catalyst of the present invention allows the operation of a continuous reforming system to be conducted at low pressure (i.e., 100 to about 350 psig.) for about the same or better catalyst life before regeneration as has been heretofore realized with conventional monometallic catalysts at higher pressures (i.e., 400 to 600 psig.). On the other hand, the stability feature of the present invention enables reforming operation conducted at pressures of 400 to 600 psig. to achieve substantially increased catalyst life before regeneration.

Similarly, the temperature required for reforming is generally lower than that required for a similar reforming operation using a high quality catalyst of the prior art. This significant and desirable feature of the present invention is a consequence of the selectivity of the trimetallic catalyst of the present invention for the octane-upgrading reactions that are preferably induced in a typical reforming operation. Hence, the present invention requires a temperature in the range of from about 800° F. to about 1100° F. and preferably about 900° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature is then thereafter slowly increased during the run to compensate for the inevitable deactivation that occurs to provide a constant octane product. Therefore, it is a feature of the present invention that the rate at which the temperature is increased in order to maintain a constant octane product, is substantially lower for the catalyst of the present invention than for a high quality reforming catalyst which is manufactured in exactly the same manner as the catalyst of the present invention except for the inclusion of the Group VI-B and Group IV-A metallic components. Moreover, for the catalyst of the present invention, the $C_5+$ yield loss for a given temperature increase is substantially lower than for a high quality reforming catalyst of the prior art. In addition, hydrogen production is substantially higher.

The reforming embodiment of the present invention also typically utilizes sufficient hydrogen to provide an amount of about 1 to about 20 moles of hydrogen per mole of hydrocarbon entering the reforming zone, with excellent results being obtained when about 5 to about 10 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory than that heretofore used with conventional reforming catalysts at no sacrifice in catalyst life before regeneration.

The following working examples are given to illustrate further the preparation of the acidic trimetallic catalytic composite of the present invention and the use thereof in the conversion of hydrocarbons. It is understood that the examples are intended to be illustrative and not restrictive.

EXAMPLE I

An alumina carrier material comprising 1/16 inch spheres was prepared by: forming an aluminum hydroxyl chloride sol by dissolving substantially pure aluminum pellets in a hydrochloric acid solution, adding hexamethylenetetramine to the resulting sol, gelling the resulting solution by dropping it into an oil bath to form spherical particles of an aluminum hydrogel, aging and washing the resulting particles and finally drying and calcining the aged and washed particles to form shperical particles of gamma-alumina containing about 0.3 wt. % combined chloride. Additional details as to this method of preparing the preferred carrier material are given in the teachings of U.S. Pat. No. 2,620,314.

A measure amount of germanium tetrachloride was dissolved in anhydrous ethanol to make a first solution. This solution was then aged and an equilibrium condition was established therein. A second solution containing water, chloroplatinic acid, ammonium tungstate and hydrogen chloride was then prepared. The two solutions were then intimately admixed and used to impregnate the gamma-alumina particles in amounts, respectively, calculated to result in a final composite containing 0.1 wt. % W, 0.2 wt. % Ge, and 0.375 wt. % Pt. In order to insure uniform distribution of the metallic components throughout the carrier material, this impregnation step was performed by adding the carrier material particles to the impregnation mixture with constant agitation. In addition, the volume of the solution was about two times the volume of the carrier material particles. The impregnation mixture was maintained in contact with the carrier material particles for a period of about ½ hour at a temperature of about 70° F. Thereafter, the temperature of the impregnation mixture was raised to about 225° F. and the excess solution was evaporated in a period of about 1 hour. The resulting dried particles were then subjected to a calcination or oxidation treatment in an air atmosphere at a temperature of about 925° F. for about 1 hour. This oxidation treatment was designed to convert substantially all of the metal moieties to the corresponding oxide forms. The calcined spheres were then contacted with an air stream containing $H_2O$ and HCl in a mole ratio of about 40:1 for about 4 hours at 975° F. in order to adjust the halogen content of the catalyst particles.

The resulting catalyst particles were analyzed and found to contain, on an elemental basis, about 0.375 wt. % platinum, about 0.2 wt. % germanium, about 0.1 wt. % tungsten and about 0.63 wt. % chloride. The atomic ratio of tungsten to platinum was 0.282:1.

Thereafter, the catalyst particles were subjected to a dry pre-reduction treatment designed to reduce substantially all of the platinum component while maintaining the tungsten and germanium components in oxidized states by contacting them for one hour with a substantially pure hydrogen stream containing less than 20 vol. ppm. $H_2O$ at a temperature of about 1000° F., a pressure slightly above atmospheric and a flow rate of the hydrogen stream through the catalyst particles corresponding to a gas hourly space velocity of about 720 hr.$^{-1}$.

EXAMPLE II

In order to compare the novel catalytic composite of the present invention with an all platinum composite of the prior art in a manner calculated to bring out the interaction of the germanium and tungsten components with the platinum component, a comparison test was made between the catalyst of the present invention, which was prepared according to the method given in Example I, and a high quality commercial reforming catalyst comprising a combination of 0.75 wt. % platinum and 0.9 wt. % chloride with an alumina carrier material. That is, the control catalyst was a combination of platinum and chlorine with a gamma-alumina carrier material, which was prepared by a method analogous to that given in Example I except for the inclusion of the germanium and tungsten components.

These catalysts were then separately subjected to a high stress evaluation test designed to determine their relative activity and selectivity for the reforming of a gasoline charge stock. In all tests the same charge stock was utilized, its characteristics are given in Table I. It is to be noted that this test is conducted under a substantially water-free condition with the only significant source of water being the 5.9 wt. ppm. present in the charge stock.

TABLE I

| Analysis Of Heavy Kuwait Naphtha | |
|---|---|
| API Gravity, at 60° F. | 60.4 |
| Initial Boiling Point, ° F. | 184 |
| 10% Boiling Point, ° F. | 205 |
| 50% Boiling Point, ° F. | 256 |
| 90% Boiling Point, ° F. | 321 |
| End Boiling Point, ° F. | 360 |
| Sulfur, wt. ppm. | 0.5 |
| Nitrogen, wt. ppm. | 0.1 |
| Aromatics, vol. % | 8 |
| Paraffins, vol. % | 71 |
| Naphthenes, vol. % | 21 |
| Water, ppm. | 5.9 |
| Octane No., F-1 Clear | 40.0 |

This test was specifically designed to determine in a very short time period whether the catalyst being evaluated has superior characteristics for the reforming process. It consists of a series of six 10 hour test periods each of which is run at a constant temperature. During each period a $C_5+$ product reformate is collected and analyzed. It was performed in a laboratory scale reforming plant comprising a reactor containing the catalyst, hydrogen separation zone, a debutanizer column, a suitable heating, pumping and condensing means, etc.

In this plant, a hydrogen recycle stream and the charge stock are commingled and heated to the desired conversion temperature. The resulting mixture is then passed downflow into a reactor containing the catalyst as a fixed bed. An effluent stream is then withdrawn from the bottom of the reactor, cooled to about 55° F. and passed to the separating zone wherein a hydrogen-rich gaseous phase separates from a liquid phase. A portion of the gaseous phase is continuously passed through a high surface area sodium scrubber and the resulting substantially water-free hydrogen stream recycled to the reactor in order to supply hydrogen for the reaction, and the excess over that needed for plant pressure is recovered as excess separator gas. Moreover, the liquid phase from the separating zone is withdrawn therefrom and passed to the debutanizer column wherein light ends are taken overhead as a debutanizer gas and a $C_5+$ reformate stream recovered as bottoms.

Conditions utilized in this test are: a constant temperature of about 973° F. for the first three periods followed by a constant temperature of about 1007° F. for the last three periods, a liquid hourly space velocity of 3.0, an outlet pressure of the reactor of 100 psig., and a mole ratio of hydrogen to hydrocarbon entering the reactor of 5.6:1. This two temperature test is designed to quickly and efficiently yield two points on the yield-octane curve for the particular catalysts. The conditions utilized are selected on the basis of experience to yield the maximum amount of information on the capability of the catalyst being tested to respond to a high severity operation.

TABLE II

| RESULTS OF ACCELERATED REFORMING TESTS | | | | | |
|---|---|---|---|---|---|
| Period No. | T, ° F. | Separator Gas SCF/bbl | Debutanizer Gas SCF/bbl | Debutanizer Gas/Total Gas Ratio | Octane No. F-1 Clear |
| Catalyst of the present invention - 0.375 wt. % platinum, 0.1 wt. % tungsten, 0.2 wt. % germanium, and 0.63 wt. % chlorine | | | | | |
| 1 | 973 | 1413 | 60 | .041 | 96.2 |
| 2 | 973 | 1379 | 57 | .040 | 94.7 |
| 3 | 973 | 1355 | 55 | .039 | 94.0 |
| 4 | 1007 | 1562 | 61 | .038 | 98.2 |
| 5 | 1007 | 1472 | 60 | .039 | 96.4 |
| 6 | 1007 | 1457 | 63 | .040 | 96.0 |
| Control catalyst - 0.75 wt. % platinum, 0.9 wt. % chlorine | | | | | |
| 1 | 973 | 1427 | 76 | .050 | 94.6 |
| 2 | 973 | 1351 | 78 | .055 | 93.0 |
| 3 | 973 | 1314 | 79 | .057 | 92.3 |
| 4 | 1007 | 1436 | 94 | .061 | 96.6 |
| 5 | 1007 | 1391 | 98 | .066 | 94.9 |
| 6 | 1007 | 1331 | 99 | .069 | 94.1 |

The results of the separate tests performed on the catalyst of the present invention and the control catalyst are presented for each test period in Table II in terms of inlet temperature to the reactor in ° F., net excess separator gas in standard cubic feet per barrel of charge (SCF/bbl), debutanizer overhead gas in SCF/bbl, the ratio of the debutanizer gas make to the total gas make, and F-1 clear octane number of the $C_5+$ product stream.

Referring now to the results, given in Table II, of the separate tests performed on these catalysts, it is evident that the effect of the combination of a germanium component with a tungsten component is to substantially promote the platinum component. That is, the catalyst of the present invention is sharply superior to the control catalyst in both activity and selectivity. As was pointed out hereinbefore, a good measure of activity for a reforming catalyst is octane number of reformate produced at the same conditions; on this basis, the catalyst of the present invention was more active than the control catalyst at both temperature conditions. However, activity is only half of the story: activity must be coupled with selectivity to demonstrate superiority. Selectivity is measure directly by reference to $C_5+$ yield and indirectly by reference to separator gas make, which is roughly proportional to net hydrogen make which, in turn, is a product of the preferred upgrading reactions, and by reference to debutanizer gas make which is a rough measure of undesired hydrocracking and should be minimized for a highly selective catalyst.

Referring again to the data presented in Table II and using the selectivity criteria, it is manifest that the acidic traimetallic catalyst of the present invention is materially more selective than the control catalyst.

It is intended to cover by the following claims all changes and modifications of the above disclosure of the present invention which would be self-evident to a man of ordinary skill in the catalyst formulation art and/or in the hydrocarbon conversion art.

I claim as my invention:

1. An acidic catalytic composite comprising a porous carrier material containing, on an elemental basis, about 0.01 to about 2 wt. % platinum group metal, about 0.01 to about 5 wt. % Group IV-A metal, about 0.01 to about 3 wt. % Group VI-B transition metal and about 0.1 to about 3.5 wt. % halogen; wherein the platinum group metal, Group IV-A metal and Group VI-B transition metal are uniformly dispersed throughout the porous carrier material; wherein substantially all of the platinum group metal is present in the elemental metallic state; wherein substantially all of the Group IV-A metal and the Group VI-B transition metal are present in oxide form; wherein the halogen component is present in the form of combined halide, and wherein the atomic ratio of Group VI-B transition metal to platinum group metal is about 0.05:1 to about 4:1.

2. An acidic catalytic composite as defined in claim 1 wherein the platinum group metal is platinum.

3. An acidic catalytic composite as defined in claim 1 wherein the platinum group metal is palladium.

4. An acidic catalytic composite as defined in claim 1 wherein the platinum group metal is iridium.

5. An acidic catalytic composite as defined in claim 1 wherein the halogen component is combined chloride.

6. An acidic catalytic composite as defined in claim 1 wherein the porous carrier material is a refractory inorganic oxide.

7. An acidic catalytic composite as defined in claim 6 wherein the refractory inorganic oxide is alumina.

8. An acidic catalytic composite as defined in claim 1 wherein the Group IV-A metal is germanium.

9. An acidic catalytic composite as defined in claim 1 wherein the Group IV-A metal is lead.

10. An acidic catalytic composite as defined in claim 1 wherein the Group IV-A metal is tin.

11. An acidic catalytic composite as defined in claim 1 wherein the Group VI-B transition metal is tungsten.

12. An acidic catalytic composite as defined in claim 1 wherein the Group VI-B transition metal is molybdenum.

13. An acidic catalytic composite as defined in claim 1 wherein the Group VI-B transition metal is chromium.

14. An acidic catalytic composite as defined in claim 1 wherein the Group IV-A metal to platinum metal atomic ratio is about 0.05:1 to about 10:1.

15. An acidic catalytic composite as defined in claim 1 wherein the catalytic composite contains about 0.05 to about 1 wt. % platinum group metal, about 0.05 to about 2 wt. % Group IV-A metal, about 0.05 to about 1 wt. % Group VI-B transition metal and about 0.5 to about 1.5 wt. % halogen.

* * * * *